July 21, 1942. R. ENGLE Plant Pat. 533
CARNATION
Filed Jan. 12, 1942
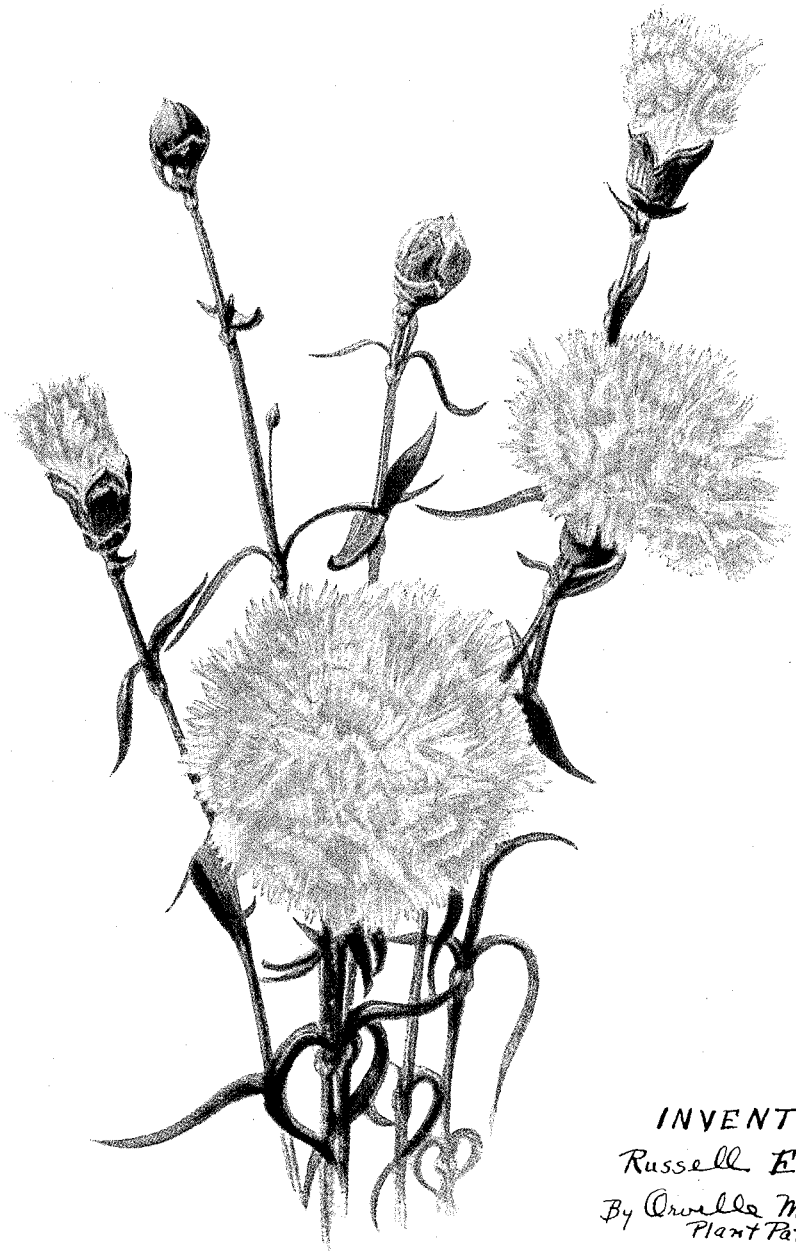
INVENTOR
Russell Engle
By Orville M. Kile
Plant Pat. Agt.

Patented July 21, 1942

Plant Pat. 533

UNITED STATES PATENT OFFICE

533

CARNATION

Russell Engle, Kokomo, Ind., assignor to Tom Knipe, Florist, Kokomo, Ind., a partnership Application January 12, 1942, Serial No. 426,509

1 Claim. (Cl. 47—60)

My present invention relates to improvements in red carnations of the large-flowered type commonly known as greenhouse forcing carnations. It was produced by crossing two unnamed seedlings which had been produced in the greenhouses of Tom Knipe, Florist. It has been asexually reproduced and its characteristics have proved to be firmly fixed.

This new variety is similar in some respects to King Cardinal and Firechief, but is very dissimilar in other respects which constitute improvements over the older varieties.

The stem and foliage is similar in all three varieties, the greatest differences being in the flower itself, particularly with reference to the blood red color, the larger petalage, the short broad calyx, and the laciniate nature of the petals of the new variety. The consistency of growth habits and production of good quality blooms are also very noticeable in this new variety.

The original illustration which is a part of this application shows in approximately true colors several specimens of the blossoms of this variety in various stages of opening, together with a portion of the stems and foliage. Following is a detailed description of the plant and flower of this new variety. Ordinary dictionary definitions of the colors are intended except where otherwise indicated.

*The plant*

Growth: Medium in height, averaging about 3 feet. Bushy, without grassiness. Unusually strong and consistent in growth. Erect. Clean. Disease resistant and tolerant of Bordeaux mixture and insecticides. Roots readily. Shows no difference between field-grown plants and those grown inside.

Flowering habit: Produces well and is consistent in producing good quality blooms.

Foliage: Moderate in quantity. Approximately Empire Green (Pl. XXXI, Ridgway Color Standards and Nomenclature), with a slight gray bloom. Leaves seldom curled and of medium width.

Stems: Same color as foliage except the usual lighter area just above the nodes. Internodes shorter than on many varieties. Strong. Stout. Long.

*The flower*

Bud: Large. Short. Bulged. Almost round just before color shows. Color blood red.

Blossom:

*Size.*—Large and very full. In the peak of the season it averages around 3½ to 4 inches in diameter.

*Form.*—High-centered. Full. Irregular. Petals curled, crinkled and tightly bunched.

*Petalage.*—From 55 to 65 petals in November, including petaloids.

*Petals.*—Very wavy and feathery. Laciniate or deeply fringed on edge. Texture and appearance much like that of tissue paper. Shape obovate, with long shank.

*Color.*—Blood red, according to Koster's Color Guide. Pure, even tone, uniformly spread over the visible portion of the petal. Does not fade.

*Calyx.*—Very broad and blunt. Exceedingly strong and tough, never known to split. Slightly over an inch in length and ⅞ inch wide. Oil Green (Pl. VI, Ridgway Color Standards and Nomenclature).

*Fragrance.*—Mild and pleasing cinnamon fragrance.

*Longevity.*—Exceptionally long-lasting.

Reproductive organs:

*Stamens.*—Few to none. Very short and insignificant. White.

*Ovary.*—Medium in size.

*Pistils.*—White with very slight pink tinge. Gracefully curved. Usually two in number. About 1½ inches long. Seldom visible in open flower.

*Comparison*

The variety which most resembles my new variety is Firechief, a sport of King Cardinal and the subject of Plant Patent No. 463. But there are many differences, especially in the flower. Some of the more important differences follow:

1. The petals of my new variety are especially laciniate, while those of Firechief are only slightly notched or serrate at the edges—in fact, much less than the average carnation.

2. Petals of my new variety are irregularly and tightly bunched and folded, while those of Firechief are much more regularly arranged and not so tightly bunched, especially the outer petals which are not crinkled but lie flat and separated from each other.

3. The form of the blossom of my new variety is less regular than that of Firechief, the outer edge of the flower of the latter being almost a perfect circle and the length of petals being more nearly uniform than in my new variety.

4. The flower of my new variety is blood red, whereas Firechief has considerable scarlet in its coloring.

5. The upper surface of the petals of Firechief has a velvety appearance, while both surfaces of the petals of my new variety appear silky. The former has somewhat the appearance of satin cloth while the latter looks more like tissue paper.

6. The difference in the petal surface produces a different sheen in the two varieties, which accounts to some extent for the difference in color effect.

7. The flowers of my new variety have a greater petalage, frequently with one-third more petals at the same season of the year and when grown under similar circumstances.

8. The calyx of my new variety is considerably shorter and wider and easily accommodates the greater petalage without splitting.

9. My new variety produces a consistent quality of perfect blooms while Firechief has many variations.

Having thus disclosed my invention, I claim:

The new and distinct variety of carnation plant herein shown and described, characterized particularly by its consistency in producing high quality blooms which have a strong, short and very broad calyx and a very full petalage of tightly folded and bunched petals of a blood red color, a tissue-paper texture and appearance, and an especially laciniate nature.

RUSSELL ENGLE.